United States Patent [19]

van den Berg et al.

[11] Patent Number: 4,835,335

[45] Date of Patent: May 30, 1989

[54] PROCESS FOR TWO-STAGE CATALYTIC CONVERSION OF AN OLEFINS-CONTAINING FEED

[75] Inventors: Johannes P. van den Berg; Pierre Grandvallet; Andras G. T. G. Kortbeek, all of Amsterdam, Netherlands

[73] Assignee: Shell Oil Company, Houston, Tex.

[21] Appl. No.: 163,045

[22] Filed: Mar. 2, 1988

[30] Foreign Application Priority Data

Mar. 3, 1987 [GB] United Kingdom ............... 8704960

[51] Int. Cl.$^4$ ................................................ C07C 1/00
[52] U.S. Cl. ..................................... 585/312; 585/251; 585/32 P; 585/517; 585/832
[58] Field of Search ............... 585/251, 517, 832, 312, 585/329

[56] References Cited

U.S. PATENT DOCUMENTS

| | | | |
|---|---|---|---|
| 3,898,296 | 8/1975 | Wideman | 585/832 |
| 4,479,023 | 10/1984 | Marty et al. | 585/832 |
| 4,520,225 | 5/1985 | Marty et al. | 585/832 |

*Primary Examiner*—Curtis R. Davis
*Attorney, Agent, or Firm*—Kimbley L. Muller

[57] ABSTRACT

A two-stage catalytic conversion process for converting an olefins-containing feed is disclosed which comprises contacting the feed in a first stage under substantially non-oligomerizing conditions with a catalyst comprising at least one metal (X) selected from the group consisting of metals from Groups 1a, 1b, 2a, 2b, 4b, 5b, 6b and 8 of the Periodic Table of the Elements and contacting the effluent from the first stage in the second stage under olefin oligomerization conditions at a temperature which is at least 50° C. above the operating temperature of the first stage with a catalyst comprising at least one metal (Z) selected from the group consisting of metals from Groups 1b, 2a, 2b, 4b, 5b, 6b, and 8 on a mordenite-type of crystalline trivalent metal (Q) silicate.

8 Claims, No Drawings

PROCESS FOR TWO-STAGE CATALYTIC CONVERSION OF AN OLEFINS-CONTAINING FEED

FIELD OF INVENTION

The invention relates to a process of two-stage catalytic conversion of an olefins-containing feed and to liquid hydrocarbons thus obtained.

BACKGROUND OF INVENTION

It is known to convert olefins having 3 or 4 carbon atoms per molecule ($C_3$ and $C_4$ olefins) in two stages in the presence of catalysts containing nickel or catalytically active metal and ZSM-5 as crystalline molecular sieve material, in order to produce dimers from olefinic feed molecules in the first stage and subsequently converting said dimers in the second stage to higher boiling hydrocarbons such as tetramers of $C_3$- or $Chd$ 4- olefins.

It is furthermore known to apply crystalline aluminum silicates (e.g. mordenite) in which one or more catalytically active metals have been incorporated, in a wide variety of hydrocarbon conversion processes, including oligomerization.

A problem associated with the use of olefins-containing feeds in catalytic processes in general, and in particular in dimerization and oligomerization processes as described herein before is the catalyst stability which is often negatively influenced by undesirable compounds such as dienes which are in many cases present in olefinic feeds available in refineries.

DETAILED DESCRIPTION OF INVENTION

Surprisingly, it has now been found that by using a metalcontaining catalyst in a first stage and a mordenite-type of catalyst carrier in combination with a catalytically active metal in a second stage under controlled conditions, liquid hydrocarbons can be prepared from an olefin-containing feed in a very stable operation.

The invention therefore relates to a process for two-stage catalytic conversion of an olefins-containing feed wherein the feed is contacted in a first stage under substantially non-oligomerizing conditions with a catalyst comprising as least one metal (X) selected from the group consisting of metals from Groups 1a, 1b, 2a, 2b, 4b, 5b, 6b, and 8 of the Periodic Table of the Elements and effluent from the first stage is contacted in the second stage under olefin oligomerization conditions at a temperature which is at least 50° C. above the operating temperature of the first stage with a catalyst comprising at least one metal (Z) selected from the group consisting of metals from Groups 1b, 2a, 2b, 4b, 5b, 6b, and 8 on a mordenite-type of crystalline trivalent metal (Q) silicate.

Reference is made to the Periodic Table of the Elements as published in the "Handbook of Chemistry and Physics", 55th edition (1975), CRC Press, Ohio, USA.

Preferably, a catalyst is used in the second stage in which the molar ratio Z:Q is greater than n⁻1, n being the valency of the metal Z.

The metals X and Z may be present in the catalysts in the form of metal compounds such as oxides or salts, or in the metallic- or ionic state.

In a preferred embodiment of the process according to the invention the metals X and Z are the same, both possessing catalytic activity for the conversion of olefinic hydrocarbons. However, since the first stage of the process is preferably carried out at a temperature from 20° C. to 150° C., in particular from 30° C. to 100° C., the extent to which oligomerization of olefins will occur is very limited in the first stage, and in some cases substantially zero. In particular at relatively low temperatures from 30° C. to 100° C. in the first stage adsorption and/or conversion of highly reactive dienes into compounds which do not quickly deactivate the second stage catalyst are thought to be the main features.

In a preferred embodiment the catalysts employed in the two stages of the process according to the invention can be the same. In a particularly preferred embodiment both stages of the present process are carried out in series flow, thus avoiding the separation of product from the first stage which is required in many known two-stage processes. Moreover, a series-flow set up has the advantage that the present two-stage process can even be carried out in a single pressure vessel, provided that a temperature profile is maintained therein in accordance with the invention e.g. by means of heat exchange internals.

The second stage of the present process is most preferably operated at a temperature which is at least 100° C. above the operating temperature of the first stage, in particular when the latter temperature is from 30°–100° C. as discussed herein before.

The second stage is preferably carried out at a temperature from 150°–330° C., a pressure from 1–100 bar and a space velocity from 0.1–10 kg feed/kg catalyst hour. Most preferably, the second stage of the process is carried out at a temperature from 180°–300° C., a pressure from 10-50 bar and a space velocity from 0.2–5 kg feed/kg catalyst hour.

Preferably, at least part of the amount, and most preferably the total amount, of metal(s) X and Z has (have) been incorporated into the catalyst by means of ion exchange. Preferably, the catalyst applied in both stages of the process according to the invention is prepared by treating a mordenite-type of carrier material, which comprises exchangeable cataions such as alkali metal-, hydrogen- and/or preferably ammonium ions, one or more times with a solution of at least one metal salt such as an aqueous solution of a metal nitrite or -acetate. The ion exchange treatment is suitably carried out at a temperature from 0° C. up to the boiling temperature of the solution, and preferably at a temperature from 20°–100° C.

The valency n of the metals Z can vary from +1 to +6. Preferably, however, at least one of the metals Z in the second stage catalyst is bivalent, in which case the molar ratio Z:Q is preferably greater than 0.5. Z is preferably selected from the group consisting of the bivalent metals copper, zinc, cadmium, magnesium, calcium, strontium, barium, titanium, vanadiaum, chromium, manganese, iron, cobalt, and nickel. A particularly preferred metal X and Z is nickel.

The trivalent metal Q which is present in the crystal structure of the mordenite-type of metal silicate catalyst carrier used at least in the second stage preferably comprises at least one metal selected from the group consisting of aluminium, iron, gallium, rhodium, chromium, and scandium. Most preferably Q consists substantially of aluminium; the resulting crystalling aluminium silicate preferably comprises a major part of mordenite and most preferably consists substantially completely of mordenite.

The molar ratio silicon : Q in the catalyst is suitably in the range from 5:1 to 100:1 and preferably in the range from 7:1 to 30:1. This ratio is in most cases substantially identical to the molar ratio Si : Q in the crystalline metal silicate employed as carrier material, except when some of the metal Q has been removed from the crystal structure during the catalyst preparation e.g. by means of acid leaching.

If desired (e.g. in order to increase the crushing strength of the catalyst particles), the carrier material and/or the ready catalyst for either one of the stages can be combined with a binder material such as (a combination of) refractory oxide(s), clay and/or carbon. Suitable refractory oxides comprise alumina, silica, magnesia, zirconia, titania and combinations thereof.

The molar ratio Z : Q in the ready catalyst is preferably from 0.6–1.5 and most preferably from 0.8–1.2 A molar ratio Z : Q of 0.5 or less for bivalent metals Z results in a catalyst which is in some cases less stable than a catalyst for which said ratio is greater than 0.5. A very high molar ratio Z : Q of e.g. more than 2 could lead to difficulties in the catalyst with a relatively low surface area and pore volume due to the very high degree of loading with metal(s) Z.

After loading of the carrier material with the metal(s) Z, the catalytically active composition thus obtained is preferably dried and calcined before being employed as catalyst in the process according to the present invention. Drying is suitably carried out at a temperature from 100°–400° C., and preferably from 110°–300° C., for a period of 1–24 hours; the calcination temperature is suitably from 400°–800° C. and preferably from 450°–650° C. The calcination treatement is suitably carried out at (sub-)atmospheric or elevated pressure for a period of 0.1–24 hours, and preferably of 0.5–5 hours in air or in an inert (e.g. nitrogen) atmosphere.

A wide variety of olefinic hydrocarbons-containing feeds can be employed in the process according to the present invention, provided that the dimensions of the olefinic hydrocarbon molecules are such that they can be catalytically converted with a mordenite type of catalyst.

Mono-olefins are preferably used as feed (components). Preferably, the feed contains more than 30% by weight of olefins having at most six carbon atoms per molecule ($C_6$- olefins) such as ethene, propene, n-butenes, isobutene, n-pentenes, isopentenes, n-hexenes and isohexenes; in addition to said olefins, aliphatic hydrocarbons such as (cyclic) paraffins, di-olefins and mono-olefins having more than six carbon atoms per molecule and/or aromatic components can be present in the feed.

Special preference is given to butene(s)-containing feeds which are suitably obtained as by-product from (fluid) catalytic cracking processes, thermal crackign processes (e.g. for the preparation of ethene), coking- and/or pyrolysis processes.

Suitable feeds for the present process can also be prepared starting from synthesis gas which is first converted into methanol and subsequently into a product substantially consisting of $C_6$- olefins. Alternatively, the synthesis gas can be converted in the presence of a Fischer-Tropsch type of catalyst into a product which in addition to paraffinic hydrocarbons contains a considerable amount of $C_6$- olefins.

The process according to the invention can be carried out in one or more fixed- , moving- and/or fluidized beds or in slurry-type of reactor; preferably, the process is carried out in two fixed bed of catalyst particles such as extrudates, pellets or spheres passing sieve openings having a width from 0.05–5 mm, and preferably from 0.1–1 mm.

The invention furthermore relates to liquid hydrocarbons prepared by a process as described herein before. Such liquid hydrocarbons include products boiling in the gasoline range (40°–150° C.), the middle distillate range (kerosene- and gasoil fractions boiling from 150°–370° C.) and in the lubricating base oil range (above 370° C.). Products boiling below the gasoline boiling range and unconverted feed, if any, are preferably separated off from the normally liquid products and can be recycled, if desired, to the first- , and more preferably the second stage.

The invention is illustrated by the following Example.

EXAMPLE (1) preparation of catalyst A.

Mordenite in the ammonium form with a molar ratio Silicon : aluminum (=Q) of 9 is ion exchanged at a temperature of 100° C. with an aqueous solution containing one mol nickel(II) acetate/-litre. The resulting catalyst has a molar ratio of nickel (=Z) : aluminum (=Q) of one, is dried at a temperature of 120° C. for 16 hours and calcined in air at a temperature of 500° C. for one hour to obtain catalyst A.

(2) preparation of liquid hydrocarbons.

EXPERIMENT 1

A gas feed mixture obtained from a catalytic cracking process and containing 54.5% by volume (v) butane, 44.6 %v butene, 0.14 %v butadiene, 3.9 parts per million (v) sulphur and 0.29 mg/1 water is led with a space velocity of 2 kg butene/kg catalyst hour through a first microflow reactor containing 2 g. of first stage catalyst A with a particle size of 0.2–0.6 mm at a temperature of 24° C. and pressure of 16 bar; subsequently the total product obtained from the first stage reactor is led with a space velocity of 2 kg butene/kg catalyst hour through a second microflow reactor containing 6 g. of catalyst with a particle size of 0.2–0.6 mm at a temperature of 215° C. and a pressure of 16 bar.

EXPERIMENT 2

A similar feed mixture as used in Experiment 1 is led under the same conditions through the second stage reactor only.

The test results are given in the following Table, in which "Activity" is defined as the number of mol. butene converged/g. catalyst hour in the second or the only reactor. For Tests Nos. 1 and 2 the activity is listed after 0.5 mol butene/g catalyst has been converted, whereas 0.8 and 1.8 mol. butene/g. catalyst has been converted in Tests Nos. 3 and 4, and 5, respectively. With Experiment 2 it is not possible to convert 1.8 mol. butene/g. catalyst due to catalyst deactivation.

TABLE

| Experiment | Test No. | Activity × 100 |
|---|---|---|
| 1 | 1 | 1.30 |
| 2 | 2 | 1.00 |
| 1 | 3 | 1.26 |
| 2 | 4 | 0.28 |
| 1 | 5 | 1.00 |

From the results given in the Table it is clear that in Experiment 1 according to the invention the catalyst is very stable whereas it stability decreases substantially in comparative Experiment 2.

What we claim as our invention is:

1. A process for two-stage catalytic conversion of an olefin-containing feed, wherein said feed is contacted in a first stage under substantially non-oligomerizing conditions, with a catalyst comprising at least one metal (X) selected from the group consisting of metals from Groups 1a, 1b, 2a, 2b, 4b, 5b, 6b, and 8 of the Periodic Table of the Elements in the presence of a mordenite catalyst carrier to produce a first stage effluent, wherein said first stage effluent is contacted in a second stage, under olefin oligomerization conditions including a temperature which is at least 50° C. higher than said non-oligomerizing conditions of said first stage, with a catalyst comprising at least one metal (Z) selected from the group consisting of metals from Groups 1b, 2a, 2b, 4b, 5b, 6b, and 8 dispersed on a mordenite crystalline trivalent metal silicate (Q).

2. The process according to claim 1 wherein said metals X and Z are the same metal.

3. The process according to claim 2 wherein said metal Z and X are nickel.

4. The process according to claim 1 wherein said catalyst of said second stage has a molar ratio Z:Q greater than $n^{-1}$, where n is the valence of Z.

5. The process according to claim 1 wherein both said first and said second stages are carried out in series flow.

6. The process according to claim 1 wherein said first stage is operated at a temperature of from 20° C. to 150° C.

7. The process of claim 1 wherein said first stage is operated at a temperature of from 30° C. to 100° C.

8. The process according to claim 1 wherein said second stage is operated at a temperature of higher than 100° C. above said temperature of said first stage.

* * * * *